(12) United States Patent
Quinn

(10) Patent No.: US 7,419,479 B2
(45) Date of Patent: *Sep. 2, 2008

(54) CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/529,646

(22) PCT Filed: Nov. 13, 2003

(86) PCT No.: PCT/US03/36297

§ 371 (c)(1),
(2), (4) Date: Nov. 16, 2005

(87) PCT Pub. No.: WO2004/045697

PCT Pub. Date: Jun. 3, 2004

(65) Prior Publication Data

US 2006/0184097 A1    Aug. 17, 2006

Related U.S. Application Data

(63) Continuation-in-part of application No. 10/295,097, filed on Nov. 15, 2002, now Pat. No. 7,048,722, and a continuation-in-part of application No. PCT/US02/36904, filed on Nov. 18, 2002.

(51) Int. Cl.
*A61M 25/00* (2006.01)
(52) U.S. Cl. .................................. 604/270; 604/523
(58) Field of Classification Search ............... 604/43, 604/270, 6.16, 101.01, 101.02, 101.03, 264, 604/96.01, 101.04, 101.05, 103.01, 103.02, 604/103.04, 523
See application file for complete search history.

(56) References Cited

U.S. PATENT DOCUMENTS 1,879,249 A    9/1932 Honsaker (Continued)

FOREIGN PATENT DOCUMENTS

DE    43 20 186 C2    12/1994

OTHER PUBLICATIONS

Moss, Gerald, PhD, MD, FACS, "Incomparable Moss® Tubes . . . (but compare with other feeding-decompression tubes anyway.)", pp. 1-2.

*Primary Examiner*—Nicholas D. Lucchesi
*Assistant Examiner*—Christopher D Koharski
(74) *Attorney, Agent, or Firm*—Brinks Hofer GIlson & Lione

(57) ABSTRACT

An enteral feeding catheter (5) that provides access to both the stomach and the jejunum for feeding, aspiration and decompression. The catheter includes a dual lumen "D" tube (30) that joins to an external "Y" connector (25) at the proximal end of the tube. The connector serves both lumens as a source for fluid or aspiration. The gastric lumen (37) and the jejunal lumen (38) of the "D" tube both connect to a transitional connector bolus in the stomach. The gastric lumen of the "D" tube joins with a lumen in the transitional bolus that communicates with a gastric port (27). The gastric port is recessed to the level of its full internal lumen, thereby providing maximum protection against occlusion and maximum area for outflow. The "D" jejunal lumen connects in the bolus with a lumen that transitions from a "D" shape to a full circle shape. The latter provides for the attachment of a smaller, round, single lumen tube that extends into the jejunum. At the distal end of the jejunal tube is a bolus (11) containing an improved port that is also recessed to the level of the floor of the internal tube lumen to provide maximum protection against occlusion and maximum area for outflow. Both the gastric port in the transitional bolus and the jejunal port in the tip bolus may include a structural arch protruding radially outwardly therefrom. An arch is effective to prevent the body segment of either bolus from bending and restricting the ports. The invention also provides for the insertion of the tube over a guidewire (21) rather than with an internal stylet, as is normally the case with nasally inserted tubes.

6 Claims, 12 Drawing Sheets

U.S. PATENT DOCUMENTS

| | | | | |
|---|---|---|---|---|
| 2,116,083 | A | 5/1938 | Rüsch | |
| 3,384,089 | A | 5/1968 | Shriner | |
| 3,547,126 | A | 12/1970 | Birtwell | |
| 3,812,860 | A | 5/1974 | Gilbert et al. | |
| 4,356,824 | A | 11/1982 | Vazquez | |
| 4,419,094 | A | 12/1983 | Patel | |
| 4,431,426 | A | 2/1984 | Groshong et al. | |
| 4,490,143 | A | 12/1984 | Quinn et al. | |
| 4,496,347 | A | 1/1985 | MacLean et al. | |
| 4,529,399 | A | 7/1985 | Groshong et al. | |
| 4,543,089 | A | 9/1985 | Moss | |
| 4,549,879 | A | 10/1985 | Groshong et al. | |
| 4,559,046 | A | 12/1985 | Groshong et al. | |
| 4,568,329 | A | 2/1986 | Mahurkar | |
| 4,576,603 | A | 3/1986 | Moss | |
| 4,583,968 | A | 4/1986 | Mahurkar | |
| 4,594,074 | A | 6/1986 | Andersen et al. | |
| 4,613,323 | A | 9/1986 | Norton et al. | |
| 4,623,327 | A | 11/1986 | Mahurkar | |
| 4,642,092 | A | 2/1987 | Moss | |
| 4,666,433 | A | 5/1987 | Parks | |
| 4,668,225 | A | 5/1987 | Russo et al. | |
| 4,671,796 | A | 6/1987 | Groshong et al. | |
| 4,685,901 | A | 8/1987 | Parks | |
| 4,692,141 | A | 9/1987 | Mahurkar | |
| 4,701,166 | A | 10/1987 | Groshong et al. | |
| 4,769,014 | A | 9/1988 | Russo | |
| 4,770,652 | A | 9/1988 | Mahurkar | |
| 4,795,430 | A | 1/1989 | Quinn et al. | |
| 4,808,155 | A | 2/1989 | Mahurkar | |
| 4,834,712 | A | 5/1989 | Quinn et al. | |
| 4,842,582 | A | 6/1989 | Mahurkar | |
| 4,900,306 | A | 2/1990 | Quinn et al. | |
| 4,944,745 | A * | 7/1990 | Sogard et al. | 606/194 |
| 4,981,471 | A | 1/1991 | Quinn et al. | |
| 5,057,091 | A * | 10/1991 | Andersen | 604/270 |
| 5,084,014 | A | 1/1992 | Picha et al. | |
| 5,160,342 | A | 11/1992 | Reger et al. | |
| 5,178,625 | A | 1/1993 | Groshong | |
| 5,197,951 | A | 3/1993 | Mahurkar | |
| 5,221,255 | A | 6/1993 | Mahurkar et al. | |
| 5,221,256 | A | 6/1993 | Mahurkar | |
| 5,242,389 | A | 9/1993 | Schrader et al. | |
| 5,269,770 | A | 12/1993 | Conway et al. | |
| 5,374,245 | A | 12/1994 | Mahurkar | |
| 5,378,230 | A | 1/1995 | Mahurkar | |
| 5,421,826 | A * | 6/1995 | Crocker et al. | 604/509 |
| 5,451,216 | A * | 9/1995 | Quinn | 604/270 |
| 5,486,159 | A | 1/1996 | Mahurkar | |
| 5,498,249 | A | 3/1996 | Quinn | |
| 5,520,662 | A | 5/1996 | Moss | |
| 5,571,093 | A * | 11/1996 | Cruz et al. | 604/270 |
| 5,599,322 | A | 2/1997 | Quinn | |
| 5,645,528 | A * | 7/1997 | Thome | 604/96.01 |
| 5,776,111 | A | 7/1998 | Tesio | |
| 5,807,339 | A | 9/1998 | Boström et al. | |
| 5,810,787 | A | 9/1998 | Quinn | |
| 5,902,285 | A | 5/1999 | Kudsk et al. | |
| 6,511,474 | B1 | 1/2003 | Andersen | |
| 7,048,722 | B2 * | 5/2006 | Quinn | 604/270 |
| 2003/0069534 | A1 * | 4/2003 | Work et al. | 604/43 |

* cited by examiner

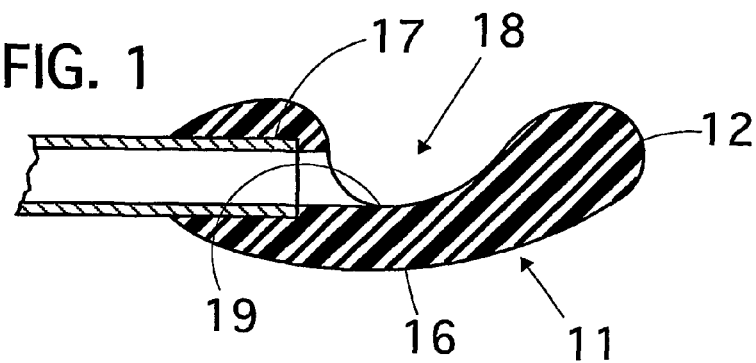
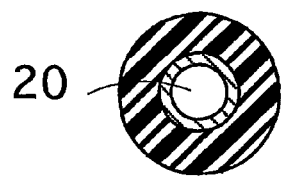
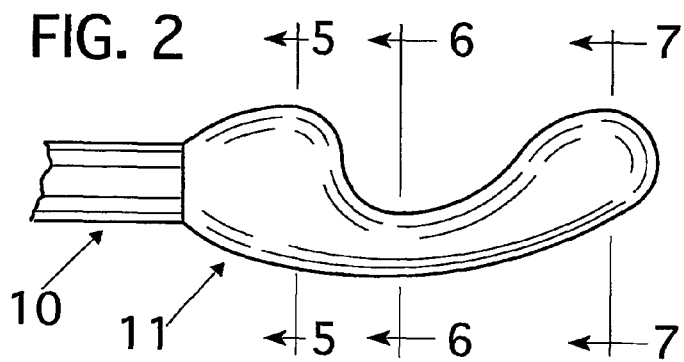
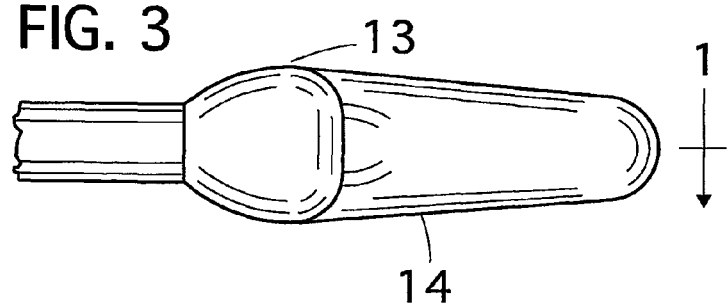
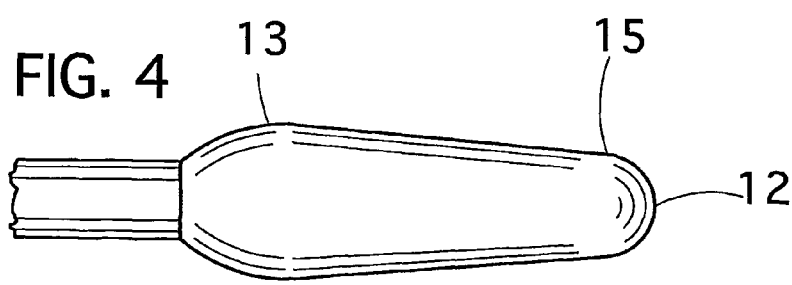

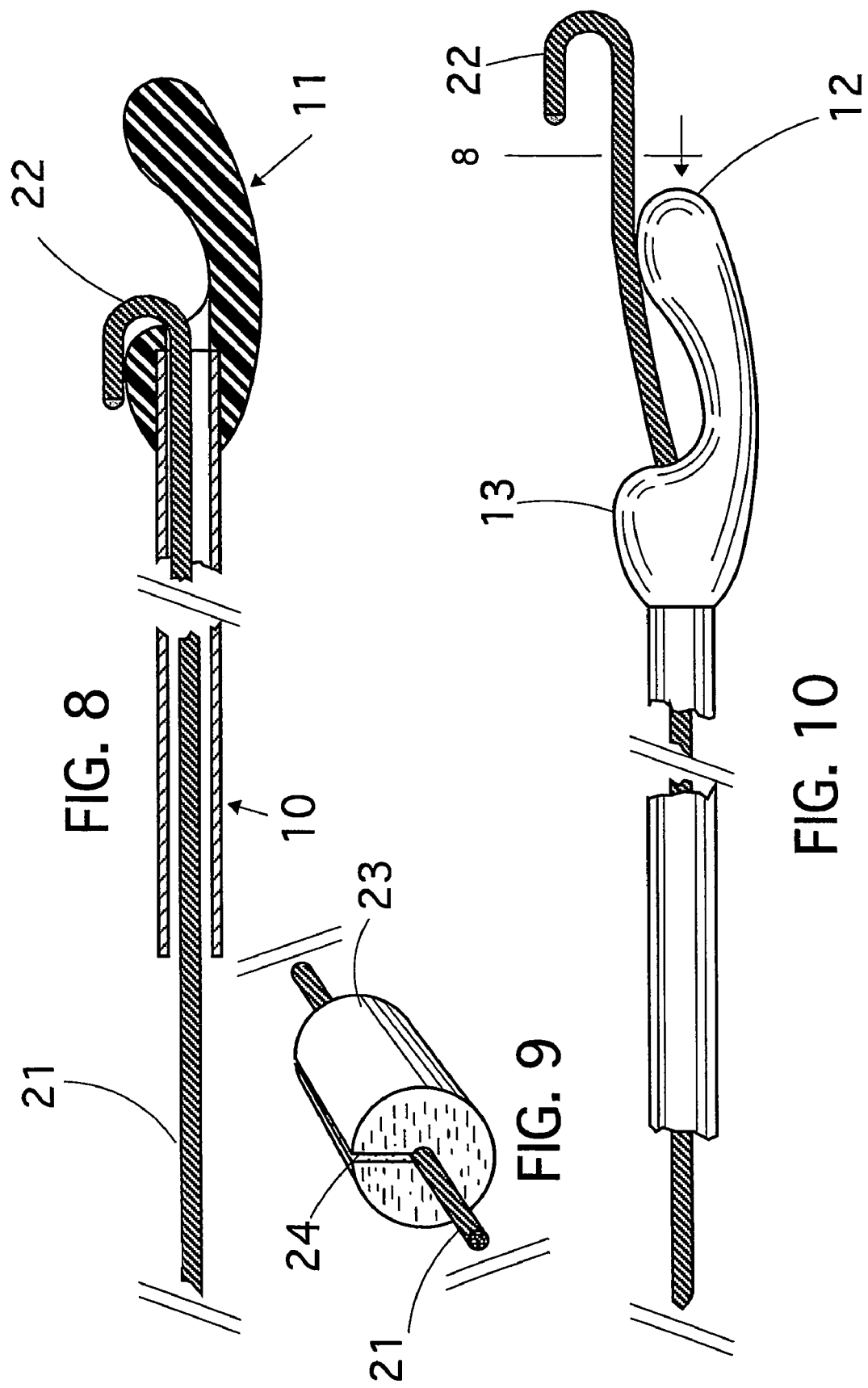

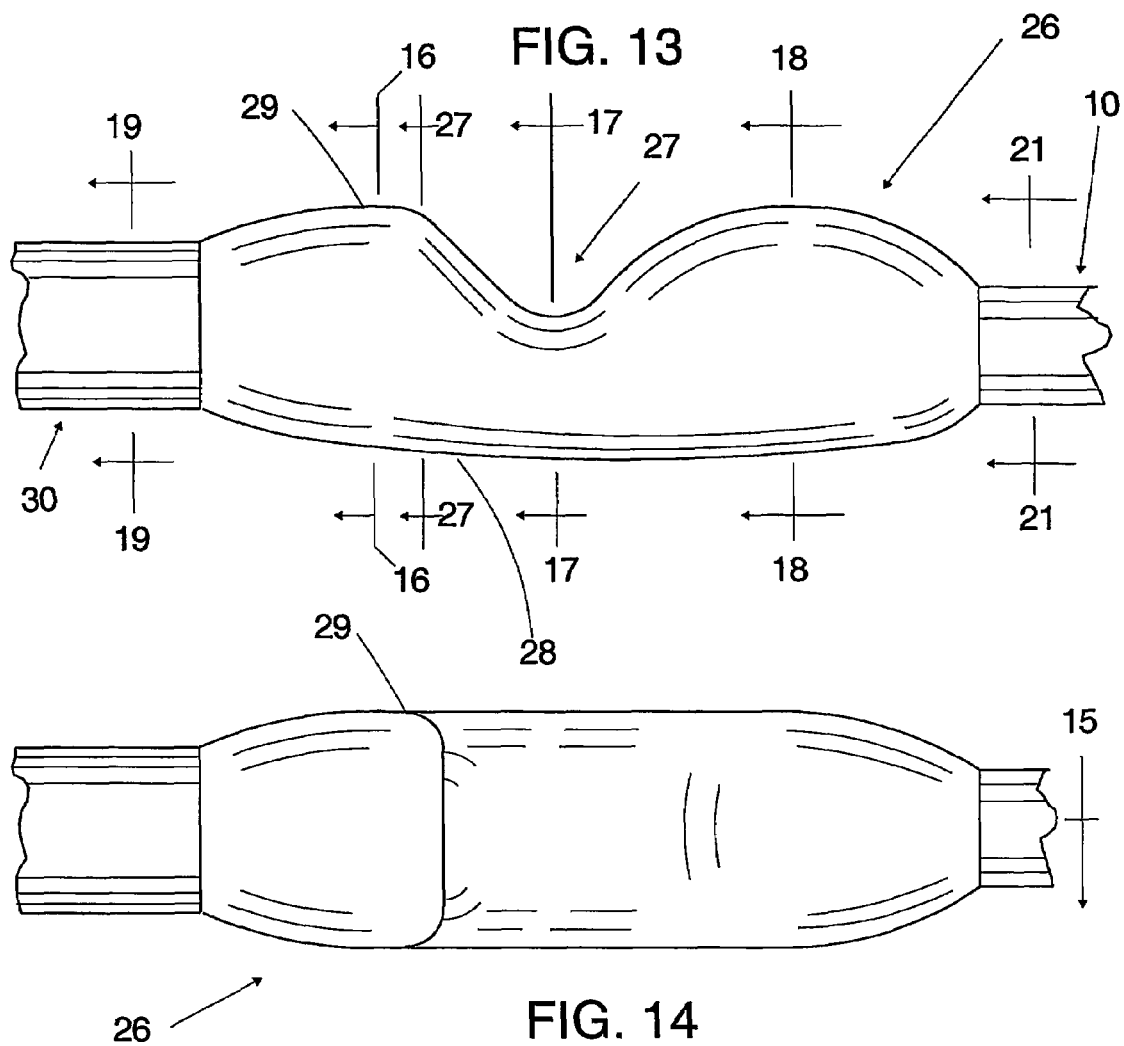
FIG. 13
FIG. 14
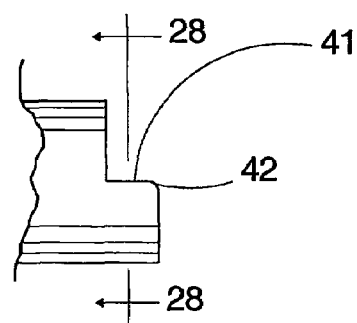
FIG. 26

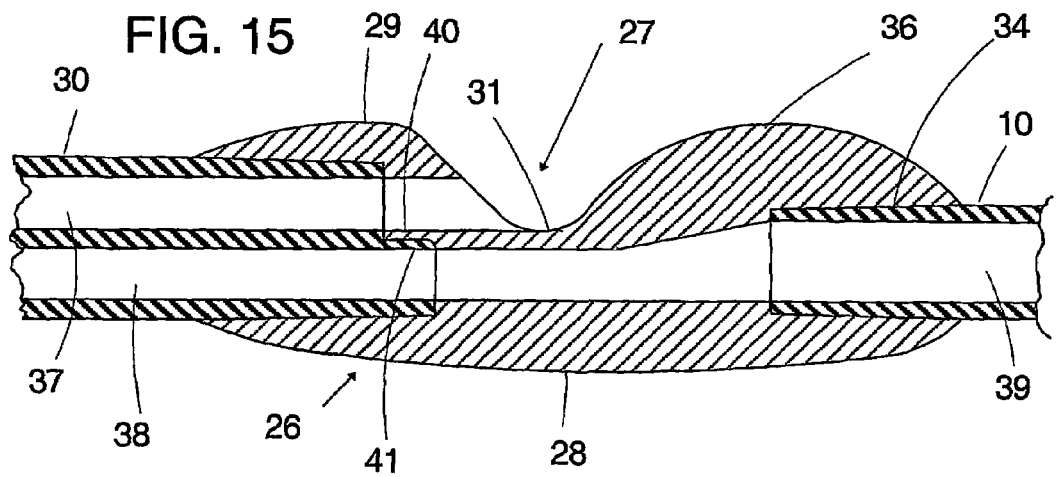
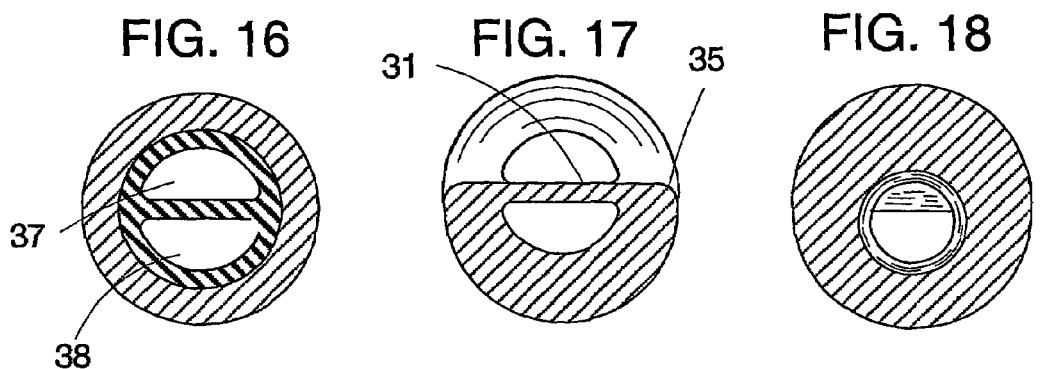
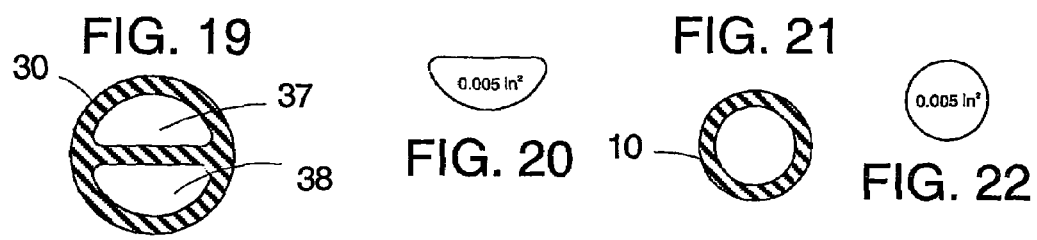
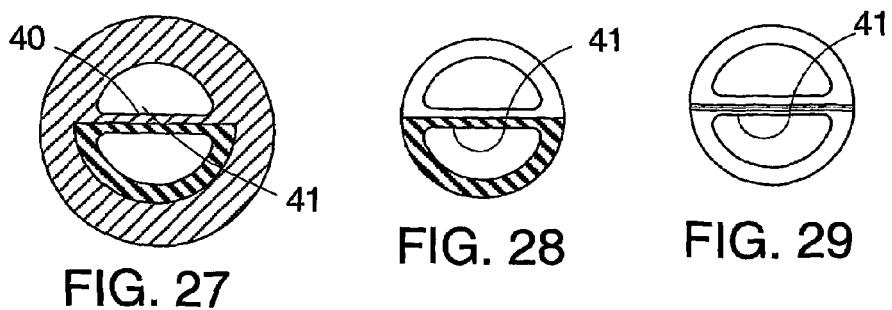

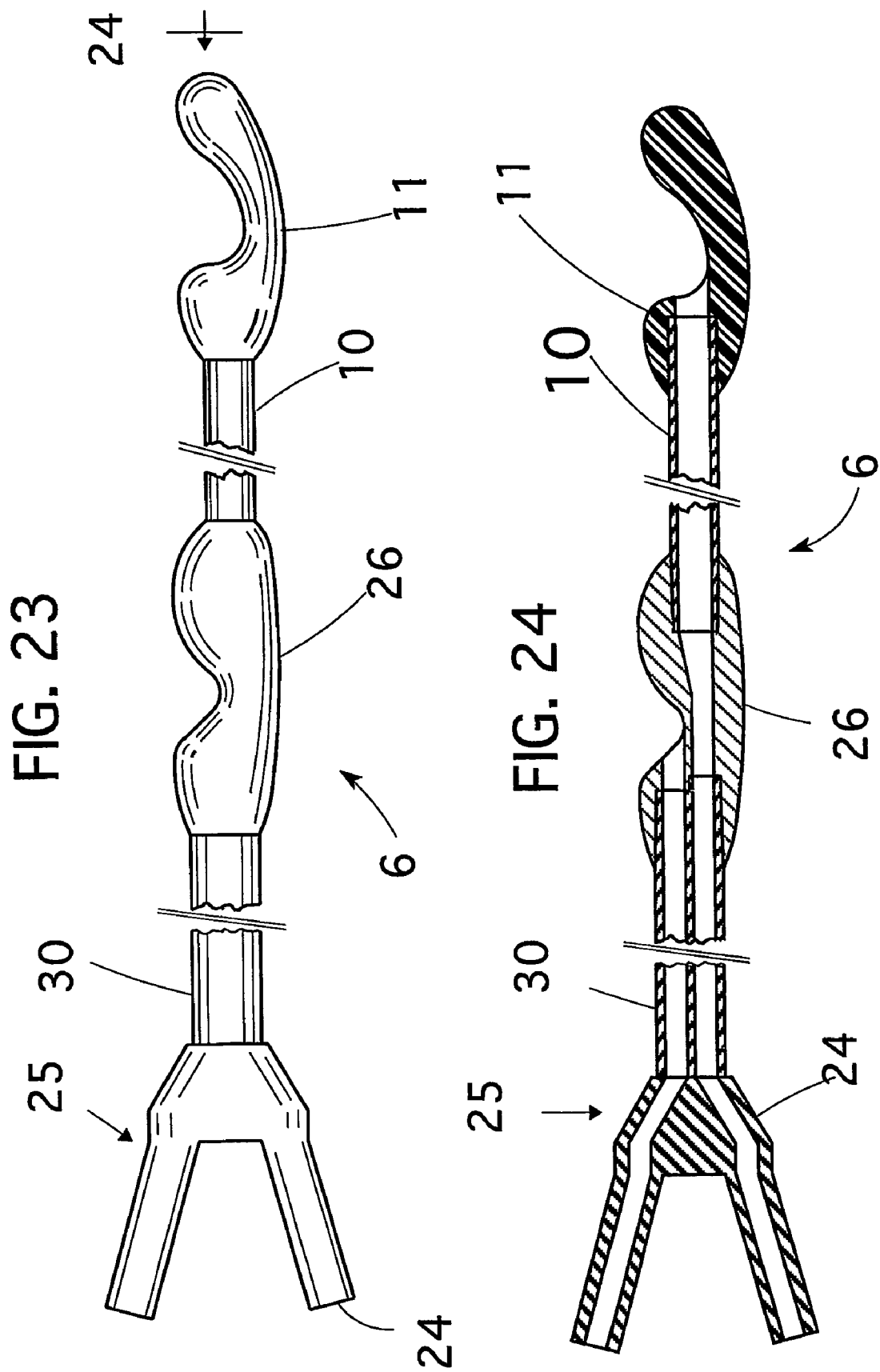

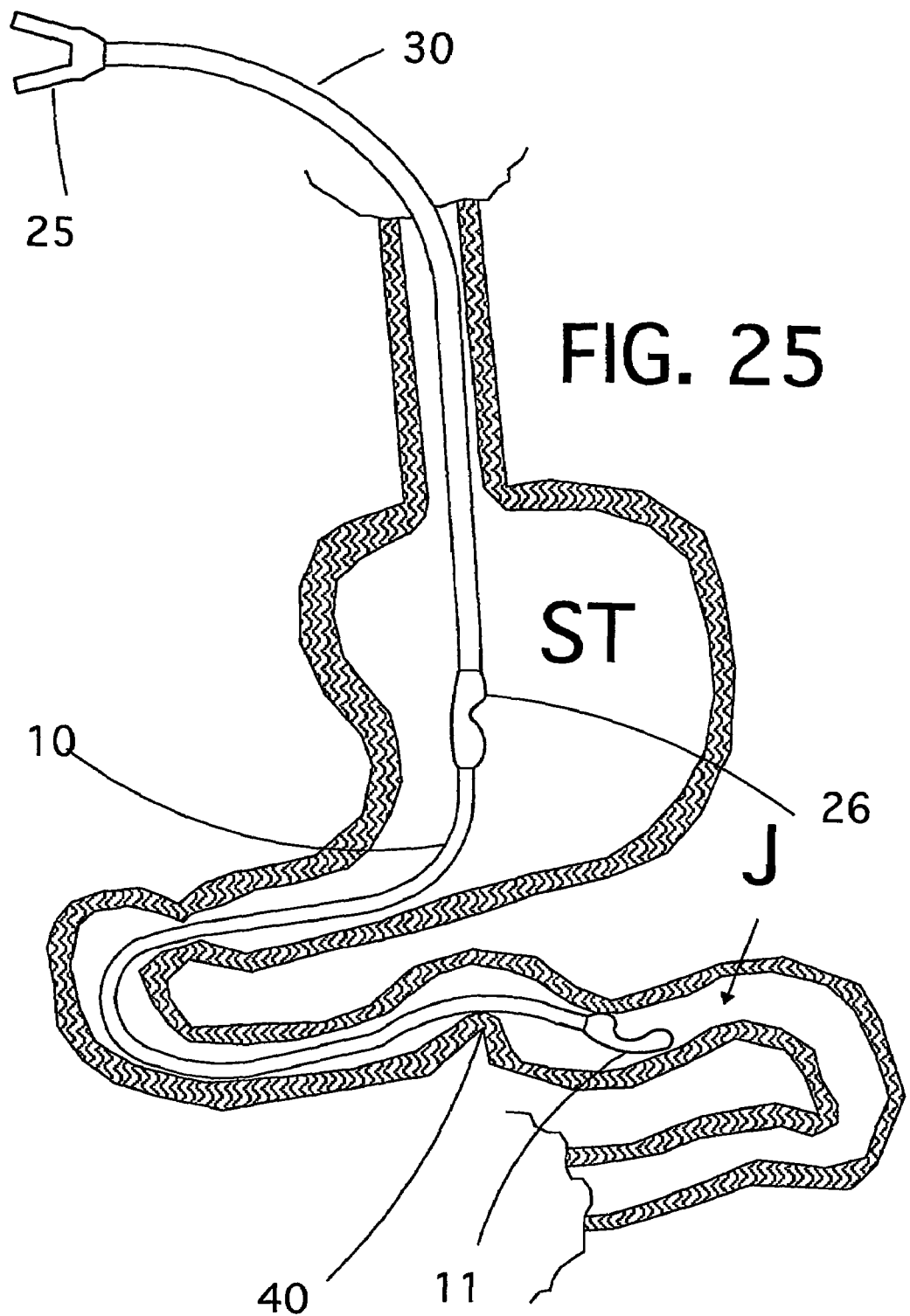

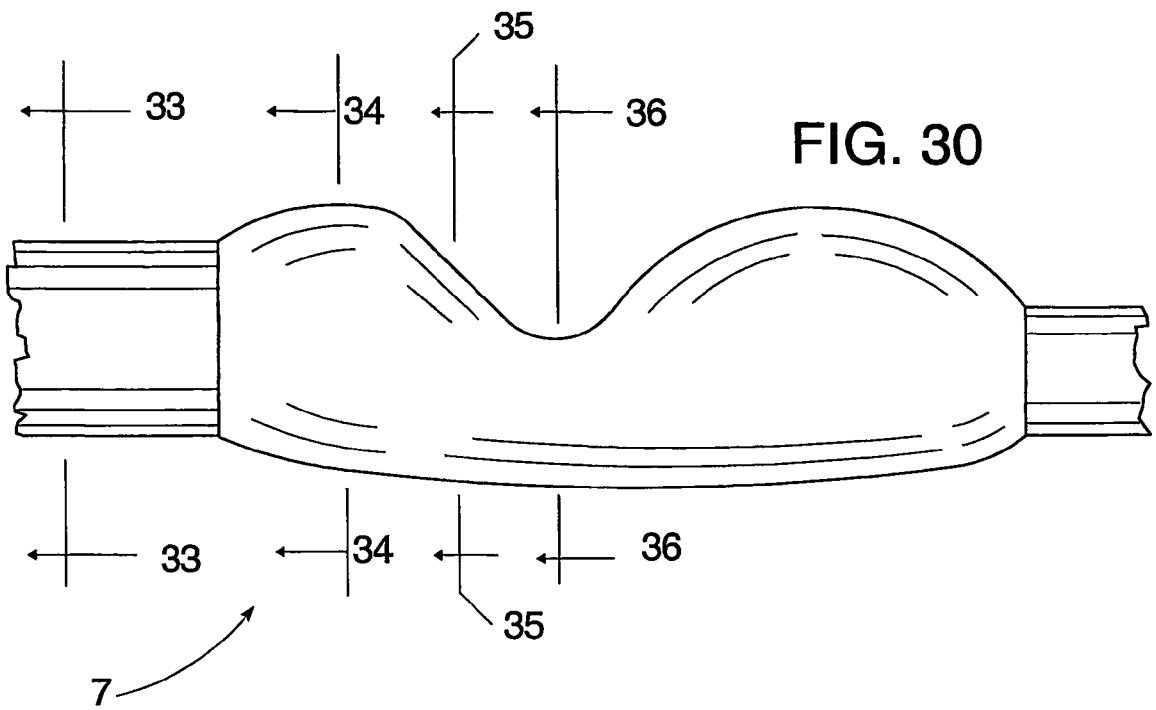
FIG. 30
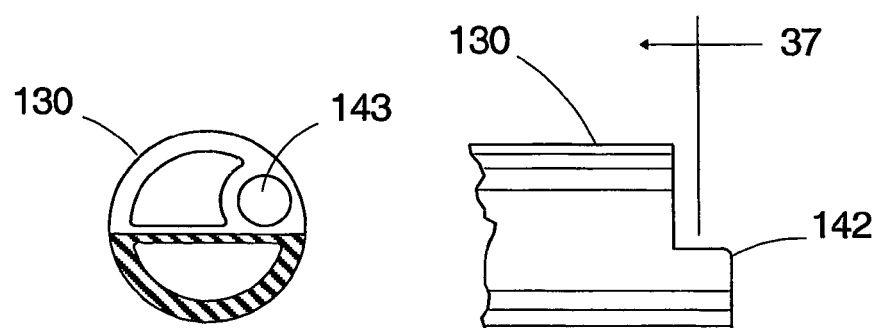
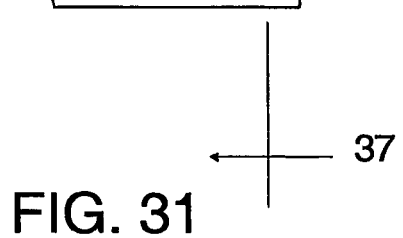
FIG. 37
FIG. 31

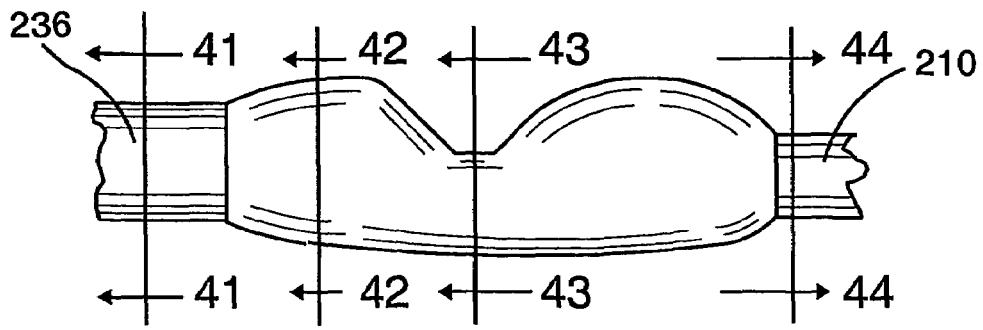
FIG. 38
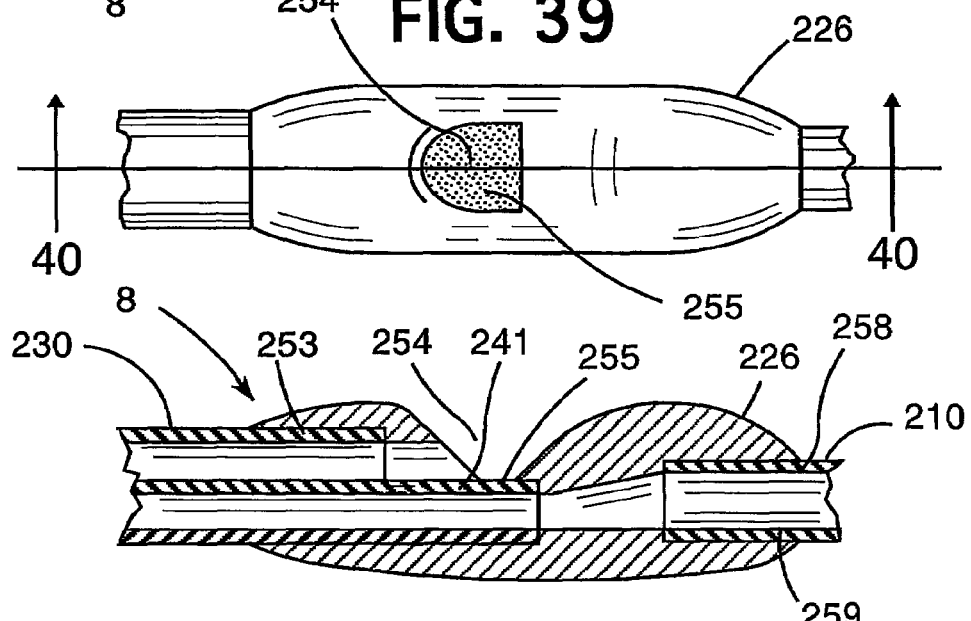
FIG. 39
FIG. 40
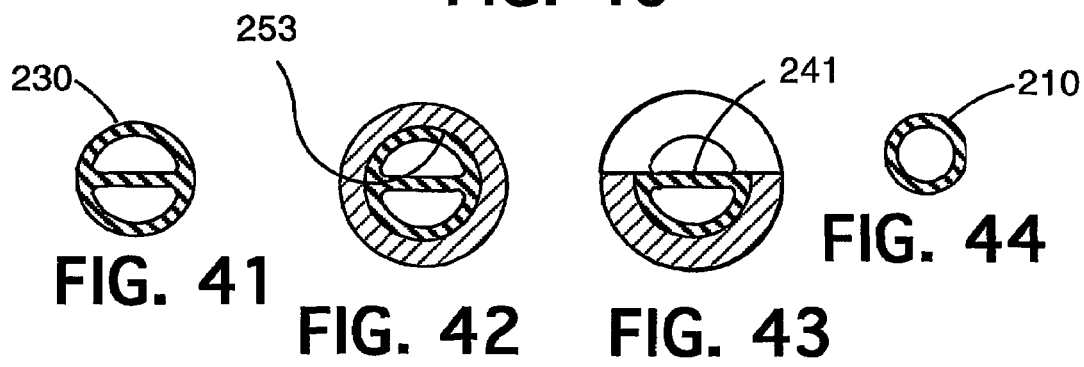
FIG. 41   FIG. 42   FIG. 43   FIG. 44

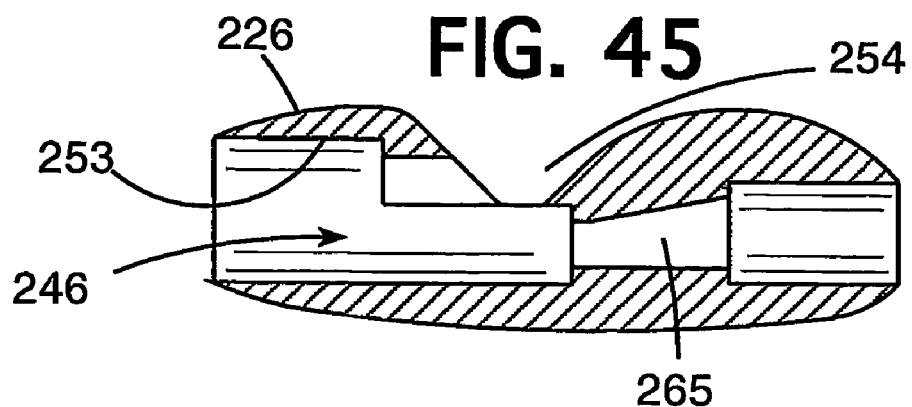
FIG. 45
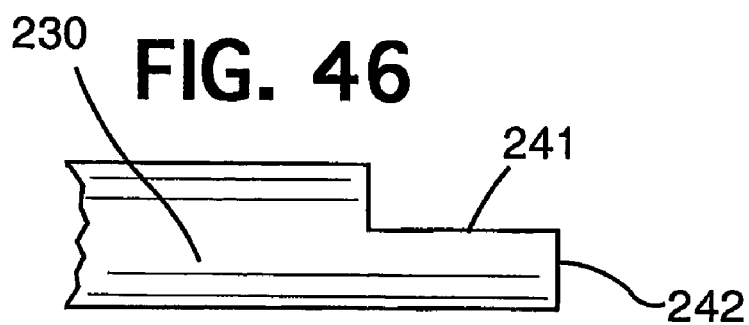
FIG. 46
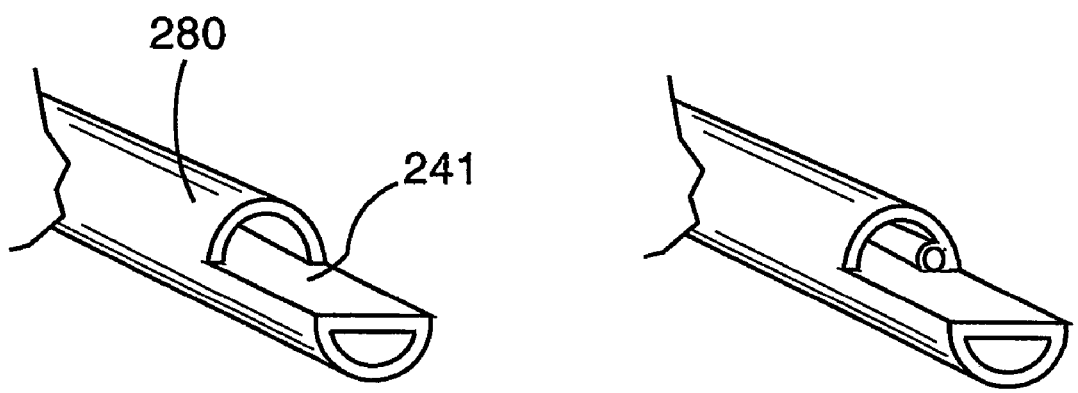
FIG. 47
FIG. 48

CATHETER

RELATED APPLICATIONS

This application is a nationalization of International Application No. PCT/US03/36297 filed Nov. 13, 2003. International Application No. PCT/US03/36297 is a continuation-in-part of U.S. patent application Ser. No. 10/295,097, filed Nov. 15, 2002, now U.S. Pat. No. 7,048,722 and of PCT Application No. US02/36904 filed Nov. 18, 2002, and claims the priority benefit of each of those applications.

FIELD OF INVENTION

This invention relates generally to catheters for use in administering fluids to body cavities, irrigating the cavities and aspirating them. It relates particularly to catheters and the distal ends thereof which contain the opening(s) for fluid egress or ingress.

BACKGROUND OF THE INVENTION

Prior art catheter and bolus inventions are disclosed in U.S. Pat. Nos. 4,594,074, 5,451,216, 5,599,322 and 5,810,787. U.S. Pat. No. 4,594,074, for example, addresses catheter bolus construction as it relates to both aspiration and outflow. The side walls of the bolus at the bolus port are recessed to a height of no more than one half of the internal diameter (ID) of the bolus passage. Lowering the walls below this minimum level would result in bending of the tube. Practically speaking, in the preferred embodiment of this particular catheter bolus, the height of the side the walls bracketing the bolus port must actually be at the full height of the bolus passage.

The three other patents referred to describe a catheter which allows the side walls of the bolus to have a height which is less than one half of the outside diameter of the body. This is accomplished by using side walls that have a continuously curving slope and by providing a body segment that includes a structural arch component protruding radially outward therefrom. This design provides a recessed, protected port that is larger than the port in the catheter bolus of Pat. No. 4,594,074 while still preventing the bolus from kinking and restricting the port.

The tip boluses disclosed in all of these patents are what are referred to as "smooth" boluses. They are glued over the tube. Usually, the socket of the bolus has walls that are 0.015 inches thick. The tip bolus is slightly larger than the tube, but only as large as is necessary to form the gluing socket. For an example, a 12FR feeding tube has an outside diameter of 0.158 inches. The OD of the 12FR smooth tip bolus is 0.188, or 0.030 larger than the tube so as to incorporate the socket walls. Thus, the bolus thickness OD is increased to slightly more than that of a 14FR tube (0.184 inches). This increase in thickness from tube to bolus is not important in a nasogastric feeding tube because the tube can easily be passed through the nose, and the size of the tube remaining in the nares is the major factor in patient comfort.

Some nasogastric feeding tube designs have tip boluses that are purposefully made much larger than the tubing for operational purposes. These designs are referred to as "large" boluses or "fat" boluses and are designed provide a shape which is ideal for gripping by peristalsis. Fat boluses are commonly attached to 8FR, 10FR and 12FR tubes and have outside diameters of 0.230 inches, which is considerably larger than even the OD of a 12FR tube, for example.

Difficulty of insertion and clogging of the catheter have heretofore restricted the use of gastric/jejunal feeding tubes or catheters. However, it is generally recognized that jejunal placement is preferred over gastric or duodenally placed catheters. Duodenal placement solves some of the problems of pulmonary aspiration, but the incidence of such aspiration is still 20%. Tubes pull out of the duodenum easily and feeding material leaks back into the stomach. In contrast, the jejunum has strong peristalsis resisting pull-out, and the curves leading to it from the stomach also help resist inadvertent removal.

SUMMARY OF THE INVENTION

An object of the invention is to provide a new and improved catheter bolus construction, a construction which allows for the elimination of the bolus sidewalls described in the aforedescribed prior art patents whereby a port is recessed to the level of the full internal diameter of the connecting tube lumen, whether the lumen has a "D" shape or a fully circular shape.

Another object of the invention is to provide an improved naso-gastric/jejunal (NGJ) catheter with gastric and jejunal ingress/egress ports that assure against clogging.

Another object of the invention is to use a fat bolus configuration and increase the size of the port by eliminating the walls, while incorporating a radially protruding structural arch component effective to prevent the bolus body from kinking and restricting the port.

Still another object of the invention is to provide for one directional flexing of the bolus forming the jejunal tip, whereby the tube can be inserted over a guidewire rather than with an internal stylet.

Yet another object is to provide a catheter which allows the tube to move over a guidewire, around bends in the intestine, into the jejunum after the guidewire has been inserted past the Ligament of Treitz by fluoroscopy.

Another object is to provide an improved NGJ catheter that can be introduced over a guidewire which is inserted via fluoroscopy.

Still another object is to provide a NGJ catheter that is of the smallest size possible while at the same time providing adequate ingress and egress of fluid from both the stomach and the jejunum.

Still another object is to provide a NGJ catheter that allows for gastric decompression.

Still another object is to provide a NGJ catheter that is simpler and easier to manufacture than those presently in use.

Yet another object of the invention is to provide methods of solvent bonding a dual lumen tube to a transitional bolus so that there is no leakage between the lumens at the junction of the parts.

Still another object of the invention is to provide methods of solvent bonding a triple lumen tube to a transitional bolus so that there is no leakage between the two main lumens while the third lumen opens to the stomach.

Another object of the invention is to provide an air inlet line in a three lumen tube so that it is adjacent to the suction line, thereby being able to balance the atmosphere in the stomach without being isolated from the suction line.

Yet another object of the invention is to protect the adjacent air and suction lines from the stomach wall by positioning them in a recessed port.

Yet another object of the invention is to provide bolus and bolus tip shapes that are identifiable by X-ray.

Yet another objective of the invention is to provide bolus and bolus tip shapes that are identifiable by "feel" by the surgeon during gastric or intestinal surgery.

The foregoing and other objects are realized in accord with the present invention by providing a catheter with a gastric transitional bolus and a jejunal tip bolus for delivering fluids to, or suctioning fluids from, body cavities of a patient. The catheter includes a dual lumen tube with a conventional, "Y" shaped connector accessing both of the "D" lumens at the proximal end of the tube. The connector is used to connect the catheter to a source of fluid or suction.

The transitional bolus incorporates a gastric port with no side walls. The jejunal port in this bolus has a passage that transitions from "D" shaped to a circular cross-section so that a single lumen, jejunal tube may be attached.

The jejunal tip bolus has a "fat" configuration. The bolus includes a port that has no side walls and provides the maximum port size to prevent occlusion in either the inflow or aspiration mode. The jejunal tip bolus has a bullet nose on its front end and is tapered from back end to front end. This configuration allows the entire bolus to flex and facilitates easy insertion over a guidewire.

Three distinct types of gastric/jejunal catheters are disclosed. The first type is a single lumen tube with a non-occluding tip. This tube has all of the characteristics of standard nasogastric feeding tube, except it is longer so that its tip can be placed into the jejunum. This version benefits from the new tip design, as do all the three versions. This tube is recommended for all routine nasogastric/jejunal feeding over gastric or duodenal placement.

The second type of catheter has a dual, "D" lumen tube as its initial, approximately 36 inches long, gastric section. Both of the "D" lumens attach to a mid-port, 0.230 inches OD bolus at the distal end of the "D" tube. One lumen accesses a gastric port in the mid-port and the other lumen accesses and transitions to an 8FR tube that continues for another approximately 20 inches to its position in the jejunum. This tube provides for jejunal feeding and also allows for the patients stomach to be aspirated and decompressed. Its usage is more limited than the single lumen type. The gastric mid-port design utilizes the recessed port features of the tip.

The third version utilizes a three-lumen tube design. Two lumens access ports in the gastric mid-port and the remaining lumen transitions to the 8FR tube that extends into the jejunum. Recent clinical studies show that early post surgical jejunal feeding helps restart peristalsis after gastric/intestinal surgery, reduces infection and promotes healing.

The practice in the United States is to place a "Salem Sump" catheter into most post gastric/intestinal surgery patients who have lost peristalsis. The "Salem Sump" catheter has two lumens. One is connected to suction and constantly evacuates the build-up of gastric fluid in the patient's stomach. The second allows air to enter the stomach so as to balance the negative pressure caused by the constant suction. The patient is fed only with IV solutions for from several days to over a week, until peristalsis returns. The three-lumen embodiment of the present invention allows enteral feeding to begin in the jejunum while also allowing constant evacuation of the stomach via wall suction. In Europe, post surgical suction is now either by intermittent syringe aspiration or by gravity. The dual lumen version of the catheter invention can be used instead.

Other commercial gastric/jejunal catheters employ an inefficient, small tube within a larger tube to access both the stomach and the jejunum. Flow through the larger tube is restricted to the space between the OD of the small tube and ID of the larger tube. This configuration results in low flow, clogging and the necessity of a very large FR (French) size outer tube.

BRIEF DESCRIPTION OF DRAWINGS

The invention, including its construction and method of operation, is illustrated more or less diagrammatically in the drawings, in which:

FIG. 1 is a longitudinal sectional view of the jejunal catheter of the invention taken along line 1-1 of FIG. 3., showing the jejunal bolus tip connected to the catheter tube;

FIG. 2 is a side view of the catheter seen in FIG. 3, showing the bolus connected to the catheter tube;

FIG. 3 is a top plan view of the catheter seen in FIG. 2;

FIG. 4 is a bottom plan view of the catheter seen in FIG. 2;

FIG. 5 is a sectional view taken along line 5-5 of FIG. 2;

FIG. 6 is a sectional view taken along line 6-6 of FIG. 2;

FIG. 7 is a sectional view taken along line 7-7 of FIG. 2;

FIG. 8 is a longitudinal sectional view through a jejunal catheter showing a guidewire in place during initial insertion through the nares when the guidewire is used as a stylet;

FIG. 9 is a perspective view of flexible plug used to trap a guidewire in the jejunal "Y" arm of the proximal connector when the jejunal catheter is placed through the nares;

FIG. 10 is an enlarged side view of the jejunal bolus during insertion showing the bolus end bent downwardly as the guidewire is advanced toward the jejunum, after the bolus is in the stomach;

FIG. 13 is a side view of a gastric/jejunal catheter including a gastric transitional bolus, showing the bolus connected to both gastric and the jejunal tubes;

FIG. 14 is top plan view of the catheter and gastric bolus seen in FIG. 13;

FIG. 15 is a sectional view taken along line 15-15 of FIG. 14;

FIG. 16 is a sectional view taken along line 16-16 of FIG. 13;

FIG. 17 is a sectional view taken along line 17-17 of FIG. 13;

FIG. 18 is a sectional view taken along line 18-18 of FIG. 13;

FIG. 19 is a sectional view of a 12FR "D" shaped tube taken along line 19-19 of FIG. 13;

FIG. 20 shows the area in square inches of a lumen of the 12FR "D" shaped lumen seen in FIG. 19;

FIG. 21 is a sectional view taken along line 21-21 of the 8FR jejunal tube in FIG. 13;

FIG. 22 shows the area in square inches of a lumen of the 8FR tube lumen;

FIG. 23 is a side view of the entire gastric/jejunal catheter, including "Y" connector, the transitional gastric bolus and the jejunal bolus;

FIG. 24 is a longitudinal sectional view through the gastric/jejunal catheter of FIG. 23;

FIG. 25 shows the gastric/jejunal catheter of the invention in place in a stomach and jejunum;

FIG. 26 is a side elevational view of the distal end of the gastric lumen seen in FIG. 15;

FIG. 27 is a sectional view taken along line 27-27 of FIG. 13;

FIG. 28 is a sectional view taken along line 28-28 of FIG. 26;

FIG. 29 is an end view of the lumen seen in FIGS. 15 and 26;

FIG. 30 is a side elevational view of another form of gastric/jejunal catheter;

FIG. 31 is a side elevational view of the distal end of the gastric lumen seen in FIG. 30;

FIG. 37 is a sectional view taken along line 37-37 of FIG. 31;

FIG. 38 is a side elevational view of yet another form of gastric/jejunal catheter embodying features of the invention with parts removed;

FIG. 39 is a top plan view of the catheter of FIG. 38;

FIG. 40 is a sectional view taken along line 40-40 of FIG. 39;

FIG. 41 is a sectional view taken along line 41-41 of FIG. 38;

FIG. 42 is a sectional view taken along line 42-42 of FIG. 38;

FIG. 43 is a sectional view taken along line 43-43 of FIG. 38;

FIG. 44 is a sectional view taken along line 44-44 of FIG. 38;

FIG. 45 is a longitudinal sectional view through the bolus seen in FIGS. 38-40;

FIG. 46 is a side elevational view of the distal end of the dual lumen catheter tube seen in FIGS. 38-43;

FIG. 47 is an end perspective view of the tube seen in FIG. 46;

FIG. 48 is an end perspective view, similar to FIG. 47, showing the triple lumen form of the tube seen in FIGS. 46 and 47;

DESCRIPTION OF THE PREFERRED EMBODIMENTS

Figure 11:
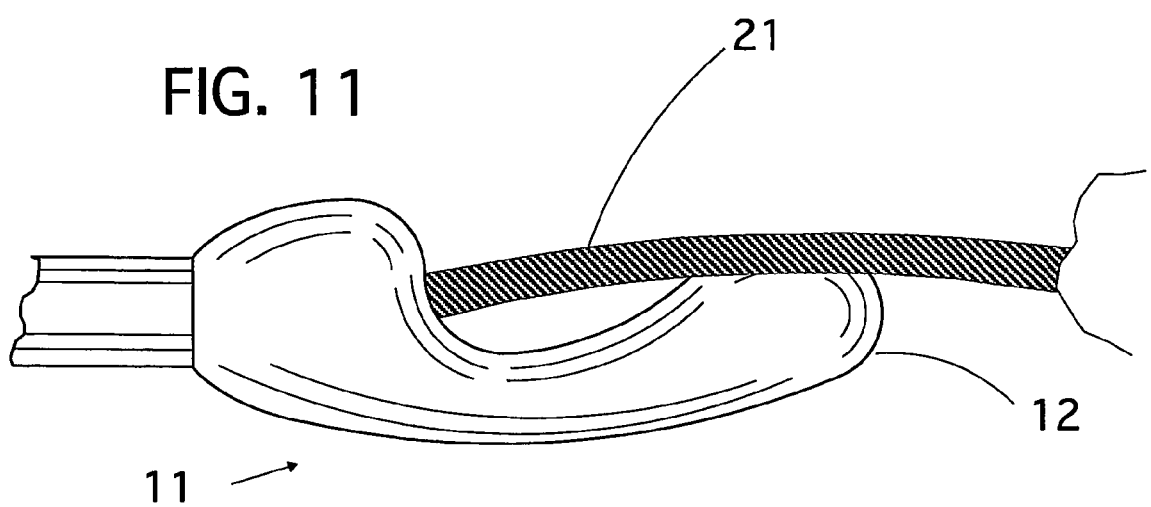
FIG. 11 is an enlarged side view of the jejunal bolus during insertion showing the position of the guidewire when the bolus follows the guidewire around a curve.

Referring now to the drawings, and particularly to FIGS. 1 through 12, a catheter 5 embodying features of the invention includes an 8FR tube 10 shown seated in a socket 17 which extends 0.185 inches into one end of a jejunal tip bolus 11.

The maximum OD of the bolus 11 is adjacent its back end, as shown at 13 in FIG. 5, and is 0.230 inches. The minimum OD of the bolus 11 is at its front end, immediately behind the bolus tip 12, as shown at 15 in FIG. 7 and is 0.152 inches. The bolus 11 is a "fat" bolus.

An enlargement or bulge 16 in the bottom of the bolus forms a structural arc opposite the port 18. The structural arc 16 prevents bending of the bolus toward the port, i.e., kinking, and subsequent occlusion of the port. The structural arc 16 extends 0.016 inches outside the normal maximum bolus OD of 0.230 inches.

As seen in FIG. 3, the bolus 11 tapers from its widest point at 13 adjacent its back end to its narrowest point at 15 behind the tip 12. This taper prevents the bolus tip 12 from bending sideways out of the configuration shown in FIGS. 3 and 4.

Although, the structural arc 16 resists bending of the bolus up and down, some flexibility in that direction is possible. This flexibility is important in the use of a guidewire.

The port 18 is open down to the floor 19 of the passage 20 through the bolus 11. In other words, the port 18 does not have side walls.

Referring to FIG. 8, a guidewire 21 is shown placed in the catheter tube 10 so that the tube 10 and bolus 11 are ready for naso-gastric insertion. A half loop 22 in the end of the guidewire 21 is seated over bolus 11 and acts as a stylet during insertion of the catheter into the stomach on the guidewire 21.

Figure 12:
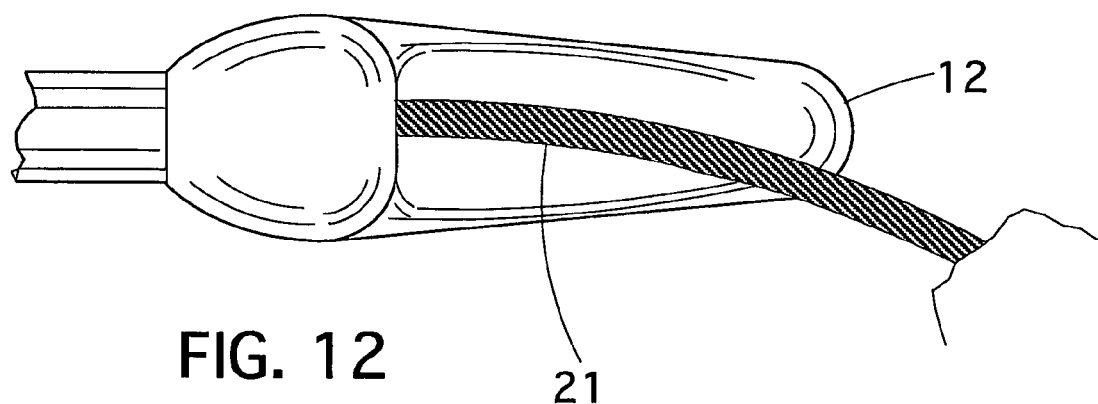
FIG. 12 is a top plan of the jejunal bolus showing the guidewire position when the bolus follows the guidewire around a curve during insertion.
Figure 32:
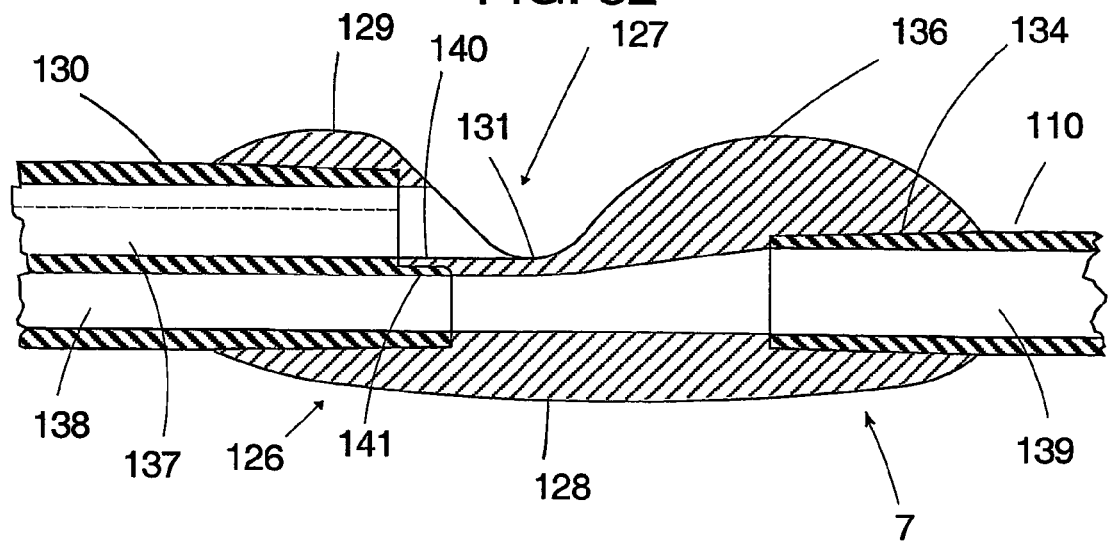
FIG. 32 is a longitudinal section through the catheter of FIG. 30.
Figure 33:
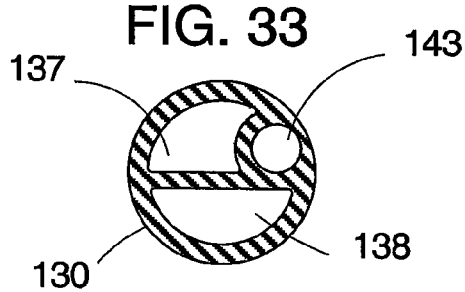
FIG. 33 is a sectional view taken along line 33-33 of FIG. 30.
Figure 34:
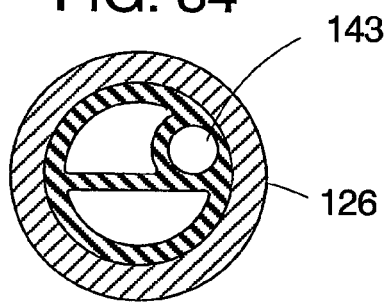
FIG. 34 is a sectional view taken along line 34-34 of FIG. 30.
Figure 35:
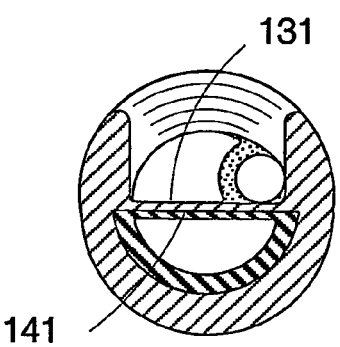
FIG. 35 is a sectional view taken along line 35-35 of FIG. 30.
Figure 36:
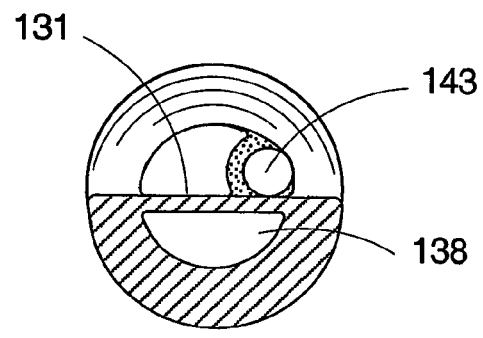
FIG. 36 is a sectional view taken along line 36-36 of FIG. 30.

FIGS. 11 and 12 show side and top plan views of the guidewire 21 position when the bolus 11 turns corners during insertion. The bolus tip 12 does not move substantially from the line of the guidewire.

During nasal insertion, it is necessary to position the guidewire so that it remains positioned correctly just behind the tip bolus 11. A flexible plug 23 shown in FIG. 9 is slipped over guidewire 21 by forcing it into slot 24. The guidewire is then positioned in the tube. The plug is forced into the connector arm serving the jejunal lumen 38. The plug 23 is compressed by the connector, thereby trapping the guidewire in its correct position in relation to the tip bolus 11.

The jejunal bolus 11 has application in all nasogastric feeding and is an improvement over all tips, including those of the afore-mentioned patents. The use of the "fat" size bolus in the catheter of the invention is the key to a number of advantages. The effective OD of the new bolus 11 is 0.230 inches for all French sizes; for example, an OD of 0.140 inches for an 8FR smooth tip, 0.168 inches for a 10FR smooth tip and 0.188 inches for a 12FR smooth tip.

For the design of the bolus 11, the recessed depth of the port 18 is 0.155 inches for the 8FR and 0.165 inches for a 10FR version. The depth is calculated by adding the radius of the OD of the bolus (always 0.115 inches) and the radius of the internal passage. The effective depth is dramatically larger than in prior art designs and offers more protection against occlusion and clogging. The outflow port 18 is fully protected while at the same time it virtually matches an open ended tube for outflow. There are no side walls to collect feeding material.

The "fat" bolus 11 design (0.230 inches OD) offers additional advantages over other "fat" boluses. Insertion is facilitated because the bolus 11 is tapered from its proximal or back end to its distal or front end and tip 12. The tip 12 has a maximum OD of approximately 0.150 inches, which is similar to the 0.140 inches tip OD of a smooth 8FR tube. This tip 12 OD is complimented by the 0.230 inches proximal OD from a safety standpoint, because clinical studies have shown that inadvertent pulmonary insertion is minimized by the use of "fat" boluses. The 0.230 inches proximal OD makes the bolus 11 too large to enter the bronchial tree. These features, combined with the ability to insert the catheter 5 over a guidewire, provide both ease of insertion and insurance against inadvertent pulmonary insertion. Effectively, the bolus presents a small, 8FR smooth bullet nose tip for ease of insertion while incorporating a "fat", trailing, tapered shape that resists entering the pulmonary tree.

The "fat" bolus also aids in the placement and confirmation of placement by flouroscopy. Both the gastric bolus (hereinafter discussed) and the jejunal bolus 11 contain 20% barium and offer thicker, more radiopaque parts to identify port placement in both the stomach and the jejunum.

Referring now to FIGS. 13-29, a first form of gastric/jejunal catheter embodying features of the invention is seen generally at 6. The catheter 6 includes a dual lumen tube 30, a gastric/jejunal bolus 26, a single lumen tube 10 and a jejunal bolus 11.

FIGS. 13 and 14 are side and top plan views of the transitional, gastric/jejunal bolus 26. The bolus 26 is tapered at 29, which is approximately where the section seen in FIG. 16 is taken. A reinforcing structural arc 28 begins at this point and extends under the bolus 26 along its length to prevent bending at the port 27. A dual lumen "D" tube 30 and an 8FR single lumen tube 10 enter the bolus 26 at opposite ends.

The floor 31 of the gastric port 27 in the bolus 26 is shown in FIGS. 15 and 17. The port 27 slopes gradually on both sides to the surface of the septum 41, which forms the jejunal "D" shaped lumen 38 below and the gastric "D" shaped lumen 37 above. The lumen 38 begins transition at 32 to a full, 8FR size oval at 33 where it is enlarged to form an 8FR size socket 34. The socket 34 is 0.185 inches deep.

In FIG. 17 the floor 31 of the port 27 is seen at the base of gastric lumen 37. The floor 31 of the port 27 extends to the edge of the tube at 35. The bolus portion distal to the port 27 has a gradual slope that reaches the same height 36 as the proximal portion of the bolus at 29.

In the dual lumen "D" tube 30, the gastric lumen 37 and the jejunal lumen 38 are identical in size. FIG. 20 shows the cross-sectional area of flow for each these lumens. FIG. 22 shows the cross-sectional area of the lumen 39 in the 8FR tube 10. Note that the cross-sectional area for flow is the same for both the gastric and jejunal lumens 37 and 38, an area of 0.005 in2.

FIGS. 15, 26, 27, 28 and 29 illustrate the method of attaching the "D" tube 30 to the midport bolus 26. The top portion of the end of the "D" tube 30 that is to be inserted into the bolus 26 is cut or ground off to a level one-half the thickness of the septum, forming flap 41. The length of the flap 41 is 0.050 inches. The bolus septum has a molded, matching flap 40. The leading, top edge of molded bolus flap 40 is ground off to assist in attachment of the bolus.

A jig (not shown) that matches the lumen 37 is inserted into the port 27 and it extends out through the end of the bolus 26. The tube 30 is dipped into solvent and is slipped over the extended jig. The tube 30 is then pushed over the jig until it seats itself in the bolus 26. In this fashion, the two flaps 40 and 41 seal in an overlapped position, eliminating any potential for leakage between the two lumens.

FIGS. 23 and 24 show the complete catheter 6. FIG. 25 shows the catheter 6 in place. The "D" tube 30 is approximately 36 inches in length. This length assures that the transitional bolus 26 is placed in the stomach, not the intestine. The jejunal 8FR tube 10 is approximately 25 inches long, which assures placement beyond the Ligament of Treitz 40. The overall length of the catheter 6 is therefore 60 inches or more when the "Y" connector 25 and the boluses 11 and 26 are included.

The jejunal bolus 11 is 0.684 inches long. The gastric bolus 26 is 0.749 inches long. The 12FR "D" tube 30 has walls that are 0.018 inches thick, the same as the septum 41. A normal 12FR single lumen feeding tube has walls that are 0.029 thick. The tube 30 can have thinner walls because the septum helps support the tube. It is also important that the tube be flexible.

An object when using the catheter 6 is to employ the largest tube possible. 8FR tubes have proven to be reliable over long periods of use. The combination of a 12FR, "D" tube and an 8FR, single lumen tube is the preferred catheter 6. However, other combinations are possible.

Referring now to FIGS. 30-37, a second form of gastric/jejunal catheter embodying features of the invention is seen generally at 7. The catheter 7 includes a triple lumen tube 130, a gastric/jejunal bolus 126, a single lumen jejunal tube 110 and a jejunal bolus 111.

The single lumen jejunal tube 110 and bolus 111 are identical to those hereinbefore described in the catheter 5. Thus, corresponding reference numerals plus 100 digits identify corresponding parts. The catheter 7 is distinguished from the catheter 6 in the construction and use of the triple lumen tube 130.

The method of connecting tube 130 and bolus 126 is similar to that in catheter 6 and is shown in FIGS. 31, 32, 35 and 37. The top of the tube 130, including a portion of third lumen 143 is ground down to one-half the thickness of the "D" septum to form a flap 141. The parts are attached in the same manner as catheter 6.

As is the case with catheter 6, both the jejunal lumen 138 and the suction lumen 137 have cross-sectional areas of 0.005 inches which is equal to an 8FR tube. The aspirating lumen 137 and the air lumen 143 both open to port 127.

The proximity of these lumens 137 and 143 to each other at the port 127 is important. The suction lumen 137, in normal usage is under constant vacuum pressure. As described before, the recessed design of port 127 prevents the suction lumen 137 from being occluded. Occlusion is also prevented because the inflow of air through lumen 143 is directly adjacent to the suction port and will always balance the pressure in the stomach. The possibility of the port 137 becoming occluded because it is isolated from the inflow of air is eliminated.

Although there is normally little tendency for fluid to back up into the air lumen 143, it may include a one-way valve in the triple lumen connector arm of lumen 143. Such a valve prevents flow from the stomach into the lumen.

Referring now to FIGS. 38-47, a third form of gastric/jejunal catheter embodying features of the invention is seen generally at 8. The catheter 8 includes a dual, "D" lumen, "D" tube 230, a gastric/jejunal bolus 226 and a single lumen jejunal tube 210 (a jejunal bolus is not shown).

The catheter 8 is distinguished from the catheters 6 and 7 hereinbefore discussed in the configuration of the dual lumen tube 230 and the bolus 226, and the manner in which they are related and assembled. Essentially, the tube 230 is configured so that when inserted into the bolus 226, it eliminates the need for a septum being formed as part of the bolus. The tube 230 effectively creates a septum for the bolus 226 when it is seated.

As seen in FIGS. 46 and 47, the top of the tube 230 is ground down to the upper surface of the "D" septum 241 for a short distance from the distal end 242 of the tube. That distance is dictated by the length of the bolus 226.

The bolus 226 is molded in the configuration seen in FIG. 45. As such, the bolus 226 has an axial passage 246 extending therethrough and a radially extending port 254 intermediate its ends, which communicates with the passage.

The passage 246, at its proximal end 251, comprises a socket 253 complementary in internal shape to the external shape of the distal end of the tube 230. As a result, when glued or sonically welded in place, as seen in FIG. 40, the septum 241 of the tube 230, where it is exposed at 255, forms the base of the port 254.

The upper lumen 261 in the dual lumen, "D"-tube 230 then communicates with the port 254 through the socket 253 above the septum 241. The lower lumen 262 communicates, through a tapering passage 265 in the bolus 226, with the single lumen jejunal tube 210. The proximal end 259 of the tube 210 is glued or sonically welded into a suitably formed socket 258 in the distal end of the bolus 226.

Referring now to FIGS. 49-53, a fourth form of gastric/jejunal catheter embodying features of the invention is seen at 9. The catheter 9 incorporates numerous features of the earlier forms of the invention but is specifically designed and constructed to function as a replacement tube catheter, i.e., a catheter which might easily be inserted through an incision in a stomach wall. As such, the catheter 9 has a maximum OD which is considerably smaller.

Figure 49:
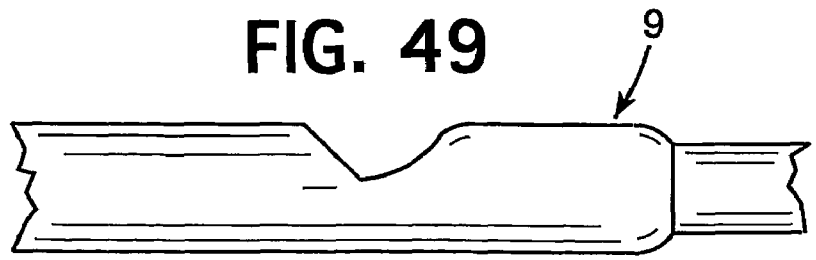
FIG. 49 is a side elevation view of still another form of gastric/jejunal catheter embodying features of the invention, with parts removed.
Figure 54:
FIG. 54 is a longitudinal sectional view through the generally semi-conical overmold used in the catheter of FIGS. 49 and 50.
Figure 52:
FIG. 52 is a longitudinal sectional view through the proximal end of the single lumen tube seen in FIGS. 49 and 50.
Figure 50:
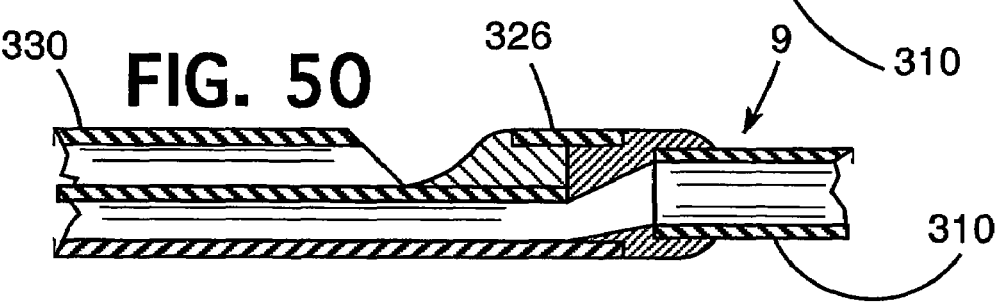
FIG. 50 is a longitudinal sectional view through the catheter of FIG. 49.
Figure 53:
FIG. 53 is a longitudinal sectional view through a generally cylindrical tube transition plug used in the catheter of FIGS. 49 and 50.
Figure 51:
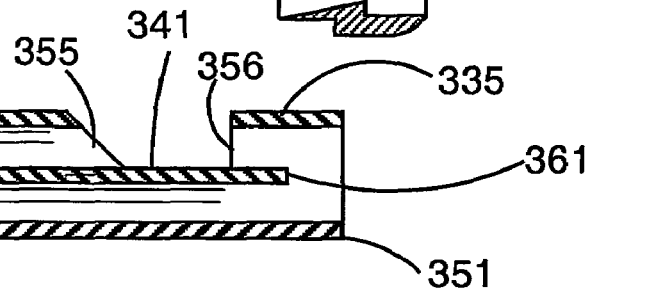
FIG. 51 is a longitudinal sectional view through the end of the dual lumen catheter tube seen in FIGS. 49 and 50.

As best seen in FIGS. 49 and 50 the catheter 9 comprises a dual lumen tube 330, a gastric/jejunal bolus assembly 326 and a single lumen jejunal tube 310 (a jejunal bolus is not shown). Unlike the boluses 26, 126 and 226 previously described, however, the bolus assembly 326 is actually a combination of three components; a modified distal end 335 of the tube 330, an end plug 336 and an overmold component 337.

In the catheter 9, the dual lumen tube 330 is utilized, at its distal end 335, as a bolus component. This accomplished by forming the distal end 335 with a semi-circular cut-out 341 above the septum 343 separating the upper lumen 345 from the lower lumen 347. The cut-out 341 is formed a short distance from the open end 351 of the tube 330.

As will be seen, the trailing edge 355 of the cut-out 341 is inclined at a 45° angle. The leading edge 356, on the other hand, extends perpendicular to the longitudinal axis of the tube 330.

The open end 351 of the tube 330 forms a socket for the plug 336, this is accomplished by cutting or grinding off the free end of the septum 343 so that it extends only half the distance between the edge 356 and the tube end 351, to the point 361.

The plug 336 is a generally cylindrical component molded of plastic. It comprises an outer end section 365 and an inner end section 367. The outer end section 365 contains an outer end socket 369 for receiving the proximal end of the single lumen tube 310. The inner end section 367 contains a transition passage 371 for communicating with the lower surface 373 which forms a seat for the overmold component 337.

The plug 336 is glued or sonically welded in the tube 330 in the position seen in FIG. 50. This combination is then overmolded with plastic to form the overmold component 337. The resulting catheter 9 is slim and perfectly suited for replacement tube insertion while still providing most of the advantages previously described for the other catheters.

Figure 55:
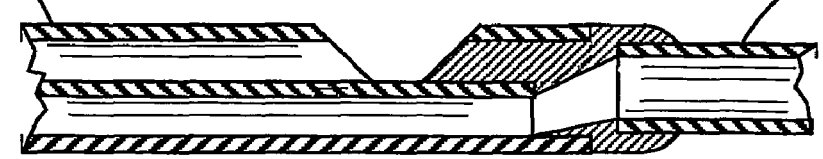
FIG. 55 is a longitudinal sectional view through a modified form of the catheter seen in FIGS. 49 and 50.
Figure 56:
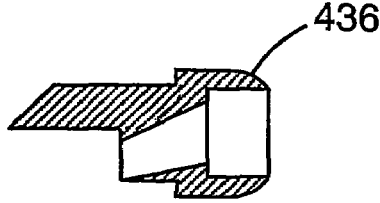
FIG. 56 is a longitudinal sectional view through a generally cylindrical tube transition plug used in the modified form of catheter seen in FIG. 55.

FIGS. 55 and 56 illustrated at 10, a modified version of the catheter 9. There, as will be seen, the insert plug 436 is configured to eliminate the need for an overmold component. The plug 436 has a shape substantially identical to that the plug 336 and overmold component 337 combined and is simply glued or sonically welded in place into the dual lumen tube 430 which is identical to the tube 330. A single lumen jejunal tube 410 is added.

Regardless of the form of gastric/jejunal catheter employed, the single lumen and the dual lumen tubes are normally inserted with an internal stylet or over a guidewire.

A triple lumen tube is usually placed during surgery by the anesthesiologist and the surgeon. With the patent's belly open, the anesthesiologist advances the tube into the stomach. The surgeon feels through the stomach wall for the shape of the tip and then "milks" the tip out of the stomach until the tip is positioned beyond the Ligament of Treitz in the jejunum. The surgeon then feels for the transitional bolus in the stomach and positions it in the stomach just outside of the pylorus, thus assuring that the bolus with its suction capability is at the lowest part of the stomach. The large shape of both the jejunal bolus and the mid-port gastric bolus assist in identifying the position of the catheter during the insertion.

The invention is described here in the context of NGJ catheters. Principles of the invention may apply equally well to other types of catheters, however, including but not limited to Foley catheters, urethral catheters and catheters for use in such diverse applications as such intravenous, pharyngeal, esophageal, rectocolonic, choledochal gastric, nasal and endobronchial procedures.

The invention claimed is:

1. A catheter for delivering fluid into, or aspirating fluid out of, a body cavity or cavities, comprising:
   a) a multiple lumen tube containing at least first and second lumens and having a proximal end and a distal end, said tube containing a septum separating said first and second lumens, said tube being formed so that said first lumen is shorter than said second lumen at said distal end whereby said second lumen opens and said septum terminates at a predetermined distance from where said first lumen opens at said distal end of said multiple lumen tube;
   b) a first bolus having a nose end and a connector end and an axial passage therethrough;
   c) said first bolus being formed independently of said multiple lumen tube and said distal end of said multiple lumen tube being seated in said axial passage at said connector end of said first bolus;
   d) only a single lumen catheter tube separate from said multiple lumen tube and seated in said axial passage of said first bolus at its nose end, said single lumen tube extending from a proximal end to a distal end and a port in said distal end; and
   e) a second bolus on the distal end of said single lumen catheter tube;
   f) said port in said distal end of said single lumen tube being formed in the side of said second bolus.

2. The catheter of claim 1 further characterized in that:
   a) said second bolus has a nose end which is bullet shaped and which is smooth and does not contain a port.

3. The catheter of claim 1 further characterized in that:
   (a) said plastic catheter tube contains a third lumen;
   (b) said third lumen extending to an opening adjacent where said first lumen opens.

4. A catheter, comprising:
   a) a catheter tube having a distal end and containing a first lumen and a second lumen separated by a septum;
   b) said distal end of said tube being formed so that said second lumen and said septum extend beyond said first lumen for a predetermined distance whereby said septum forms a substantially flat outer wall of said tube for said predetermined distance;
   c) a bolus formed independently of said multiple lumen tube, said bolus being connected to said distal end of said tube, said bolus forming at least a portion of each of a first port extending radially of said catheter over said substantially flat outer wall, said first port and communicating with said first lumen, and a second port communicating with said second lumen;

d) said septum, where it forms said outer wall of said tube, underlying at least a portion of said first port;

e) said catheter tube including a generally cylindrical wall containing said lumens, a portion of said cylindrical wall adjacent said distal end of said catheter being removed to expose said substantially flat outer wall;

f) said second lumen extending to an opening at said distal end of said tube;

g) said first lumen extending to an opening at a predetermined distance from said distal end of said tube; and h) said bolus including an attachment section fastened to said septum where it comprises an outer wall and has a rear face defining a ramp including a surface inclined at an angle to said septum.

5. The catheter of claim 4 further characterized in that:

(a) said ramp extends rearwardly to an intersection with said first lumen opening.

6. The catheter of claim 4 further characterized is that:

a) said catheter tube contains a third lumen;

b) said third lumen extending to an opening adjacent said first lumen opening.

\* \* \* \* \*

UNITED STATES PATENT AND TRADEMARK OFFICE
CERTIFICATE OF CORRECTION

PATENT NO. : 7,419,479 B2
APPLICATION NO. : 10/529646
DATED : September 2, 2008
INVENTOR(S) : David G. Quinn Page 1 of 1

It is certified that error appears in the above-identified patent and that said Letters Patent is hereby corrected as shown below:

In column 12, claim 5, line 6, before "said ramp extends" delete "(a)" and substitute --a)-- in its place.

In column 12, claim 6, line 8, after "characterized" delete "is" and substitute --in-- in its place.

Signed and Sealed this

Twenty-sixth Day of May, 2009

JOHN DOLL
*Acting Director of the United States Patent and Trademark Office*